(12) United States Patent
Poon et al.

(10) Patent No.: US 6,835,084 B2
(45) Date of Patent: Dec. 28, 2004

(54) MEDICALLY IMPLANTABLE ELECTRICAL CONNECTOR WITH CONSTANT CONDUCTIVITY

(75) Inventors: Daniel Poon, Westminster, CA (US); Peter J. Balsells, Newport Beach, CA (US)

(73) Assignee: Bal Seal Engineering Co., Inc., Lake Forest, CA (US)

( * ) Notice: Subject to any disclaimer, the term of this patent is extended or adjusted under 35 U.S.C. 154(b) by 0 days.

(21) Appl. No.: 10/366,912

(22) Filed: Feb. 14, 2003

(65) Prior Publication Data

US 2003/0157846 A1 Aug. 21, 2003

Related U.S. Application Data

(60) Provisional application No. 60/357,360, filed on Feb. 15, 2002.

(51) Int. Cl.[7] .............................................. H01R 13/627
(52) U.S. Cl. ........................................ 439/349; 439/352
(58) Field of Search ................................. 439/349, 352, 439/366; 277/644, 626

(56) References Cited

U.S. PATENT DOCUMENTS

| 4,893,792 A | 1/1990 | Balsells |
| 5,108,078 A | 4/1992 | Balsells |
| 5,139,243 A | 8/1992 | Balsells |
| 6,257,594 B1 * | 7/2001 | Halling et al. ............... 277/644 |

* cited by examiner

Primary Examiner—Chandrika Prasad
(74) Attorney, Agent, or Firm—Walter A. Hackler

(57) ABSTRACT

A medically implantable electrical connector includes a housing having a bore with an internal V-groove or a flat bottom groove therein along with radial garter spring disposed in the V-groove or an axial garter spring disposed in the flat bottom groove. A pin is provided and sized for insertion in the housing bore. The housing, spring and pin are formed from a combination of medically implantable materials in order to control electrical resistivity between the housing, the garter spring and the pin.

20 Claims, 3 Drawing Sheets

MEDICALLY IMPLANTABLE ELECTRICAL CONNECTOR WITH CONSTANT CONDUCTIVITY

This application claims the benefit of Provisional Application No. 60/357,360 filed Feb. 15, 2002.

The present invention is directed to medically implantable electrical connectors and is more particularly directed to medical connectors which have tailored connect and disconnect forces. Such connectors can be used in a number of medical devices such as, for example, pace makers defibrillators, and neuro-stimulators. Medically implantable electrical connectors are adherently different than a vast majority of other electrical connections due to the environment and critical nature of their use. Such medical connectors must not only be made of materials suitable for implanting within a body, but also must provide positive and unvarying conductivity thereacross in order to insure reliability of a functioning medical device.

Heretofore, implantable electrical connectors have utilized a lead wire, or pin, and a housing with the lead wire removably fixed to the housing by a set screw. It should be appreciated that such set screws are small, thus losable. In addition, a set screw is very torque sensitive and requires a tool for installation.

The present invention provides for an implantable electrical connector with reduced resistivity and reduced resistivity variability under static and dynamic loading without the necessity of an installation tool.

SUMMARY OF THE INVENTION

A medically implantable electrical connector in accordance with the present invention generally includes a housing having a bore with an internal groove therein along with a garter spring disposed in a groove.

A pin is sized for insertion into the housing bore and may include an external groove for capturing the spring in order to removably latch the pin within a housing bore.

Reduced resistivity across the connector including the housing spring and pin is achieved through the use of a shaped V-groove and by forming the housing, spring and pin from a combination of medically implantable materials in order to control the resistivity. Preferably, the spring is formed from platinum iridium.

In one embodiment of the present invention, the pin does not include the external groove and the housing groove is a V-groove. More particularly, the V-groove may have an included angle of about 135° and in the embodiment including the pin groove a cross-section of the pin groove may include a flat center portion subtended by angled sides. As hereinafter described a V-groove with a radial spring provides for greater conductivity of the connector with enhanced conductivity stability than a flat bottom groove with a radial spring.

Still more particularly, the angled sides may be disposed at about a 45° with a flat center.

In all of the embodiments of the present invention, one of the housing pin, or spring is preferable formed from platinum iridium with the most preferred being a platinum iridium spring. The remaining components, namely the housing and pin may be formed from MP35N or titanium grade-5 or stainless steel.

Other embodiments of the present invention include a connector with a housing V-groove and a radial garter spring, or a connector with a housing flat groove and an axial spring. The axial spring provides for greater conductivity with a housing with flat grooves in view of the fact that the axial spring motion produces a scraping action that removes oxides thus decreasing resistivity.

BRIEF DESCRIPTION OF THE DRAWINGS

The present invention will be better understood by reference to the accompanying drawings, in which.

DETAILED DESCRIPTION

Figure 1A:
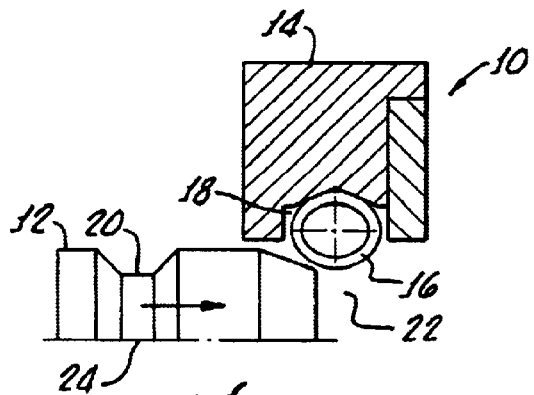
FIG. 1 is a view of one embodiment of the present invention, in partial cross section, generally showing a housing having a V-groove, a spring disposed therein along with a pin having a external groove.
FIGS. 1b–1f show the embodiment of FIG. 1a in stepwise illustration of insertion, connect-latch, and disconnect in one direction and connect latch and disconnect in an opposite direction.
Figure 1B:
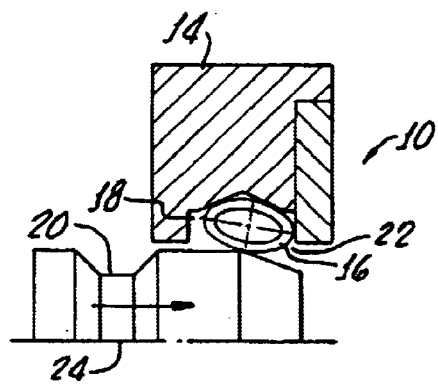
Figure 1C:
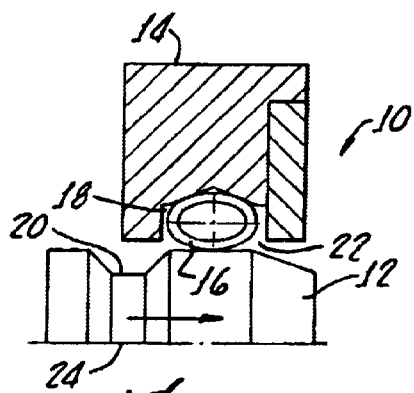
Figure 1D:
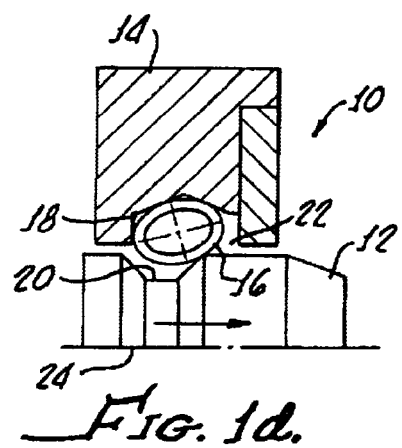
Figure 1E:
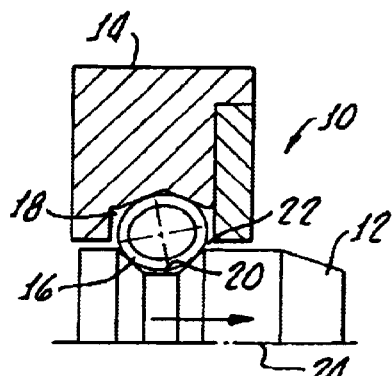
Figure 1F:
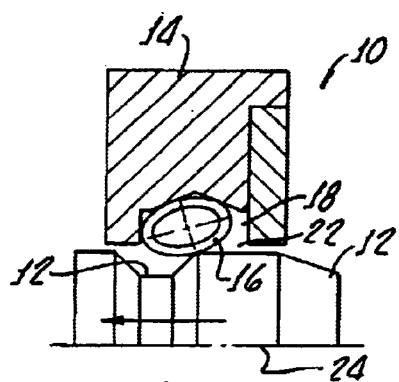

In general, two types of connectors will be hereinafter described. One type is for latching as shown in FIGS. 1a–1f in which the connector 10 includes a pin 12 retained in a housing 14 by a spring 16 within a bore 22 (See FIG. 1b), only one half of the pin 12 and housing 14 being shown as indicated by a centerline 24.

Figure 2A:
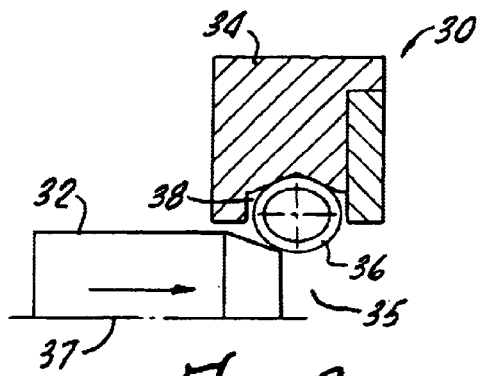
FIGS. 2a–2d show an alternative embodiment of the present invention in stepwise connect and disconnect fashion as shown in FIGS. 1a–1f utilizing a non-grooved pin.
Figure 2B:
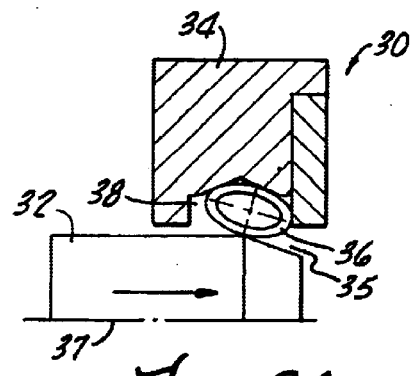
Figure 2C:
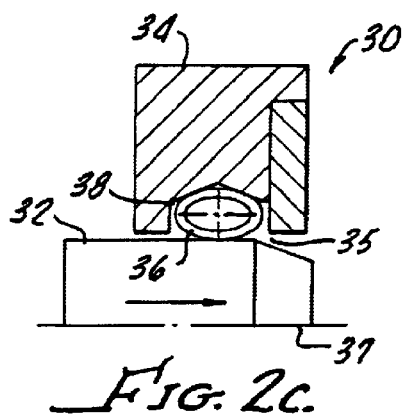
Figure 2D:
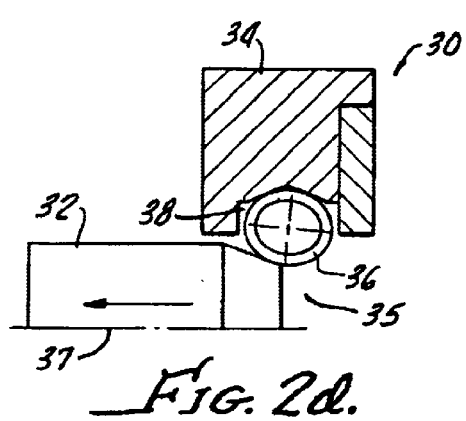
Figure 3A:
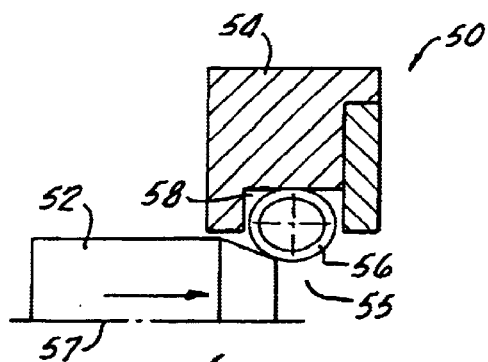
FIGS. 3a–3d illustrate yet another alternative embodiment of the present invention utilizing a housing having a flat bottom and a grooveless pin and further showing stepwise insertion and disconnect of the pin from the housing.
Figure 3B:
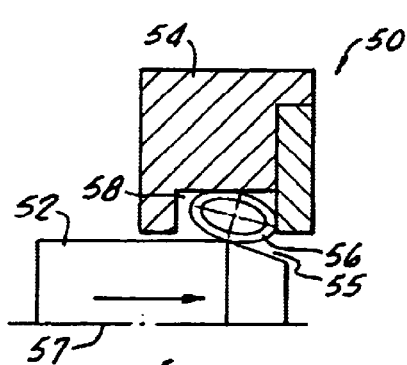
Figure 3C:
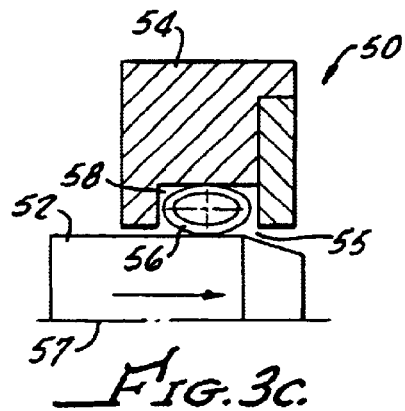
Figure 3D:
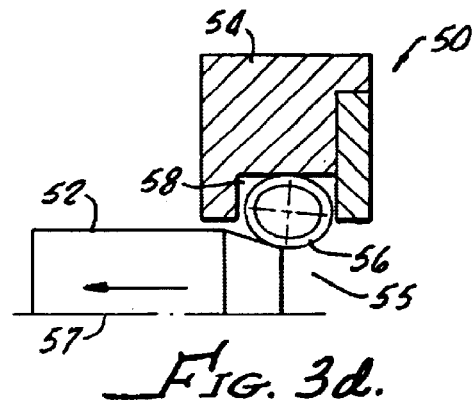
Figure 4A:
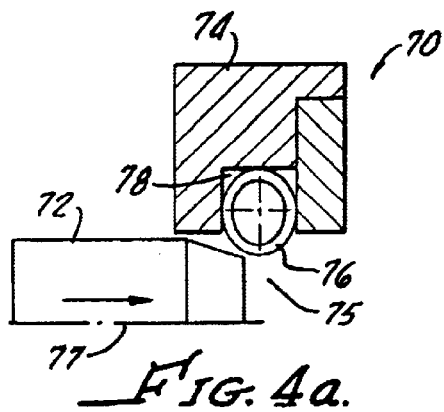
FIGS. 4a–4d show a further alternative embodiment of the present invention similar to that shown in FIGS. 3a–3d except the radial spring of FIGS. 3a–3d is replaced with an axial spring 76.
Figure 4B:
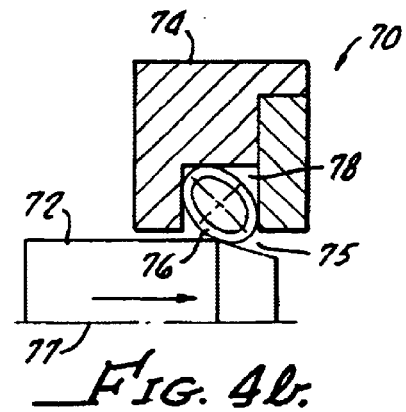
Figure 4C:
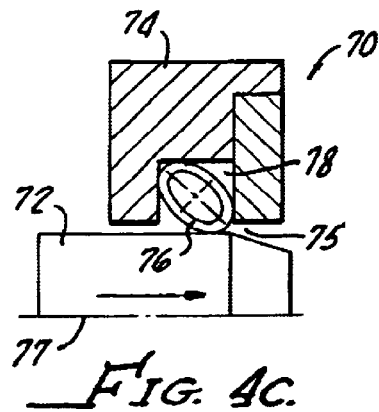
Figure 4D:
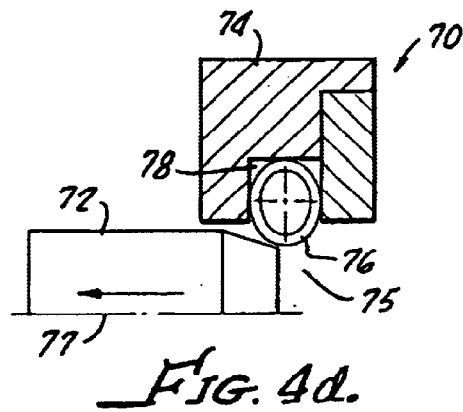

Shown in FIGS. 2a–2d, 3a–3d and 4a–4d are connectors 30, 50, 70 for holding pins 32, 52, 72 within respective housings 34, 54, 74 with bores 35, 55, 75 by the friction force derived by compressing a canted coil spring 36, 56, 76. Similar to FIGS. 1a–1f only one half of the pins 32, 52, 72 and housings 34, 54, 74 are shown as indicated by centerlines 37, 57, 77.

The springs 16, 36, 56, 76 may be radial canted coil springs 16, 36, 56, with a housing V-groove 15, 38, or axial canted coil springs 76 with a flat bottom-housing groove 78. It has been found that axial springs are preferable for a flat bottom housing groove 78 inasmuch as there is a greater coil density, i.e. more coils per arcuate distance, disposed against the pin and a scraping motion of the axial spring 76 removes oxides.

The springs 16, 36, 56, 76 may be inserted clockwise or counterclockwise with a back angle on the inside or the outside. Suitable springs are taught in U.S. Pat. Nos. 5,108, 076, FIGS. 1–6, U.S. Pat. No. 4,893,795, FIGS. 4, 5a, 5b, 5c, 5d, 5e, 6a, and 6b and U.S. Pat. No. 5,139,243, FIGS. 1a, 1b, 2a, and 2b to Balsells. All of these patents are to be incorporated herewith for teaching suitable spring designs for the present invention.

The springs 16, 36, 56, 76 are generally made with an outside diameter slightly larger than the housing groove I.D.s so that upon assembling the spring 16, 36, 56, 76 into the grooves 18, 38, 58 and 78 it creates interference with the outside diameter of the spring and the inside diameter of the housing groove 18, 38, 58, 78. With regard to springs 16, 36, 56, the interference provides a radial compression load that retains the spring 16, 36, 56 in the housing 14, 34, 54. The springs 16, 36, 56, 76 may be inserted clockwise or counter clockwise.

With regard to the spring 76, the interference provides an axial compression load that retains the spring 76 within the housing 74. In this manner, the springs 16, 36, 56, 78, are firmly retained in place. It also insures conductivity between the outside diameter of the spring 16, 36, 56, 76 and the housing 14, 34, 54, 74.

As hereinabove noted, resistivity is a very important factor since the greater the resistivity the more electrical energy is dissipated as heat across the connector 10, 30, 50, 70, which is drawn from a battery. (not shown), thus, limiting the life of the battery.

It has been discovered that by utilizing a V-groove 18, 38 substantially lower resistivity is achieved with a radial spring compared with a flat bottom groove with a radial spring. At the same time, with a V-type groove 18, 38 the spring 16, 36 is more constrained resulting in more consistent resistivity and less shuttling occurs.

The area of contact between the springs 16, 36 coils and the housing 14, 34 also effects the resistivity. The greater the area of contact of the springs 16, 36 with the housing 14, 34, the lower the resistivity.

It should be appreciated that it is very important that during operation, the resistivity, or conductivity, remains constant. The geometry of the spring 14, 84 and groove 18, 38 minimizes the amount of movement that may occur.

Connector 10 provides for latching. That is, the pin groove 20, when aligned with the housing groove 18 with the spring 16 therebetween, provides latching action as well as conductivity. At the same time such V-grooves 18 in the housing 14 assures consistent retention and resistivity.

It should be appreciated that while FIGS. 1a–1f illustrate the spring 16 being retained in the housing 14, the spring 16 may also be retained on the pin 12.

The type of V-groove 18, as hereinabove noted, effects the position, constraint of the spring and reduces the variability of resistivity. The V-groove 18 and the housing 14 may have various angles less than 180° to an included angle of about 135° or 90°, among others as shown in FIGS. 1a–1f and FIGS. 2a–2d. It has been found that a 45° (90° included angle) constrains the coils, allows good retention in the coils and provides reduced resistivity.

Increasing the deflection of the coils will tend to increase the force. The increase in force will reduce resistivity and increase the constraint of the spring 16, 36, 56, 76 minimizing the variability of resistivity, especially under dynamic loads. The force may be varied by various manners, such as, for example, the back or front angle of the coils, wire diameter, ratio of coil height to wire diameter among others. All these parameters are discussed in the hereinabove referenced U.S. Patents which have been incorporated herewith.

The ratio of disconnect to connect force can be controlled within a ratio of about 1 to 1 to about 10 to 1. With a high disconnect to connect force ratio conductivity is maintained.

A number of condition for providing force ratios include:

1. Directional. Higher ratio when the pin contacts the front angle first on insertion. This is indicated by the black dot on the coil along the major axis at insertion or disconnect and the direction of insertion.

2. Higher disconnect to connect ratios are obtained when the centerline of the coil along the major axis is closer to the pin or shaft load point.

3. The following parameters also affect the force differential:
   a. Ratio of coil height to wire diameter.
   b. Ratio of coil width to coil height.
   c. The back and front angle of the coil.
   d. The coil height.
   e. Coil width.
   f. Wire diameter.
   g. Material properties of the material, such as tensile, elongation, and modulus of elasticity.
   h. The location of the centerline of the coil along the major axis relative to the pin or shaft load point.
   i. The geometry of the housing.
   j. The spring orientation.

Flat bottom groove with axial spring compared to flat bottom groove with radial spring. These are two differences that are very important. Axial spring is compressed at assembly along the minor axis of the coil and in doing so increases the force acting on the walls of such groove and the more the squeeze between the coil height and the groove width the higher the radial force that is generated. This affects the radial force required to pass the pin through the housing contacting the spring. Such added force has an effect on the conductivity and resistivity that is not linear.

The referenced patents also discuss the relationship between the angles of the pin, angles on the housing and shape of the coil, be it round or elliptical, such that it maximizes the area of contact between group services and the spring coils.

Operation in the stepwise manner of inserting the pins 12, 32, 52, 72 and the housings 14, 34, 54, 74 for latch or resistive hold are shown in a stepwise manner in FIGS. 1a–1f, 2a–2d, 3a–3d and 4a–4d respectively.

It has been discovered that combining different materials of construction for the connection 10, 30, 50, 70 provides a method for substantially effecting the resistivity of the connectors 10, 30, 50, 70. Materials for medical applications must be of the type that are stable in implant applications, such as, for example, stainless steel type 316L, MP35N, platinum-iridium, titanium and others.

It has been unexpectedly found that the use of platinum iridium in the pin 12, 32, 52, 72, housing 14, 34, 54, 74, or spring 16, 36, 56, 76 reduces resistivity. This is particularly the case when the spring is formed of platinum iridium. The housing 14, 34, 54, 74 and pin 12, 32, 52, 72 may be formed from another material such as MP35N or titanium grade-5. With all of these materials the surface finish of the mating parts effects resistivity with the better the surface condition, the more intimate contact between mating parts and the lower force that is required to maintain resistivity.

Table 1 shows condensed data on resistivity of different types of groove springs and materials all made with a common dimensions.

TABLE 1

CONDENSED DATA ON RESISTIVITY OF DIFFERENT TYPES OF GROOVES, SPRINGS AND MATERIAL

| Item | Material | | | Flat Bottom-RADIAL Resistance Ω | V-Bottom RADIAL Resistance Ω | % Variation Between Flat Bottom Radial and V-Bottom | Flat Bottom AXIAL Resistance Ω | % Variation Between Flat Bottom Radial and Flat Bottom Axial |
|---|---|---|---|---|---|---|---|---|
| No. | Housing | Spring | Pin | Average Value | Average Value | Radial | Average Value | Axial |
| 1 | PT-IR | MPN | MPN | 0.320 | 0.203 | 36.7% | 0.127 | 52.6% |
| 2 | TNM5 | MPN | MPN | .671 | 0.488 | 27.2% | 0.296 | 137.9% |
| 3 | MPN | MPN | MPN | 1.964 | 1.065 | 45.7% | 0.590 | 300.3% |
| 4 | S.S. | MPN | MPN | 2.611 | 1.496 | 42.7% | 0.860 | 410.1% |

NOTE: Data Sorted by Average V-Bottom Housing Resistance

In Table 1 the symbol S.S. is a stainless steel type 316L, PT-IR is platinum-iridium, MPN is MP35N and TNM-5 is titanium grade-5.

As shown in Table 1 when using an axial spring 76 a groove 78 the lowest resistivity is produced in each case. The next lowest resistivity is achieved when using a radial spring 16 in a V-bottom groove 18. The reduction in percentage of resistivity between a flat bottom groove 58 with a radial spring 56 and a V-bottom groove 38 with a radial spring 36 along with a flat bottom groove 78 with an axial spring 76 illustrates a significant advantage in the selection of groove and spring types.

However, it is important to recognize that the use of platinum iridium leads to lowest resistivity of the connectors 10, 30, 50, 70.

Although there has been hereinabove described specific electrical connectors with conductivity means for holding and latching in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclose herein. Accordingly, any and all modifications, variations or equivalent arrangements which may occur to those skilled in the art, should be considered to be within the scope of the present invention as defined in the appended claims.

What is claimed is:

1. A medically implantable electrical connector comprising:
   a housing having a bore with an internal V-groove therein;
   a radial garter spring disposed in said V-groove; and
   a pin sized for insertion into the housing bore;
   said housing, spring and pin being formed from a combination of medically implantable materials in order to control electrical resistivity between said housing, said garter spring and said pin.

2. The connector according to claim 1 wherein said pin includes an external groove for capturing said spring in order to removably latch said pin within the housing bore.

3. The connector according to claim 1 wherein said V groove has an included angle of about 135°.

4. The connector according to claim 1 wherein the pin includes a groove with a flat center portion subtended by angled sides.

5. The connector according to claim 4 wherein said angled sides are disposed at about a 45° angle with said flat center.

6. The connector according to any one of claims 1–5 wherein one of said housing, said garter spring and said pin is formed from platinum iridium.

7. The connector according to claim 6 wherein said housing and pin are formed from MP35N.

8. The connector according to claim 6 wherein said housing and pin are formed from titanium grade-5.

9. A medically implantable electrical connector comprising:
   a housing having a bore with an internal flat bottomed groove therein;
   an axial garter spring disposed in said groove; and
   a pin sized for insertion into the housing bore;
   said housing, spring and pin being formed from a combination of medically implantable materials in order to control electrical resistivity between said housing, said garter spring and said pin.

10. The connector according to claim 9 wherein the pin includes a groove with a flat center portion subtended by angled sides.

11. The connector according to claim 10 wherein said angled sides are disposed at about a 45° angle with said flat center.

12. The connector according to any one of claims 10–11 wherein one of said housing, said garter spring and said pin is formed from platinum iridium.

13. The connector according to claim 12 wherein said housing and pin are formed from MP35N.

14. The connector according to claim 12 wherein said housing and pin are formed from titanium grade-5.

15. A medically implantable electrical connector comprising:
   a housing having a bore with an internal V-groove therein;
   a radial garter spring disposed in said V-groove; and
   a pin sized for insertion into the housing bore, said pin including an external groove for capturing said spring in order to removably latch said pin within the housing bore, said latch providing a disconnect force and a connect force; and said housing, spring and pin being formed from a combination of medically implantable materials in order to control electrical resistivity between said housing, said garter spring and said pin.

16. The connector according to claim 15 wherein a ratio of disconnect force to connect force is between about 1 to 1 and about 10 to 1.

17. The connector according to claim 16 wherein said V groove has an included angle of about 135°.

18. The connector according to any one of claims 15–17 wherein one of said housing, said garter spring and said pin is formed from platinum iridium.

19. The connector according to claim 18 wherein said housing and pin are formed from MP35N.

20. The connector according to claim 18 wherein said housing and pin are formed from titanium grade-5.

* * * * *

(12) EX PARTE REEXAMINATION CERTIFICATE (9784th)
United States Patent
Poon et al.

(10) Number: US 6,835,084 C1
(45) Certificate Issued: Aug. 1, 2013

(54) MEDICALLY IMPLANTABLE ELECTRICAL CONNECTOR WITH CONSTANT CONDUCTIVITY

(75) Inventors: Daniel Poon, Westminster, CA (US); Peter J. Balsells, Newport Beach, CA (US)

(73) Assignee: Bal Seal Engineering Co., Inc., Foothill Ranch, CA (US)

Reexamination Request:
No. 90/012,027, Nov. 29, 2011

Reexamination Certificate for:
Patent No.: 6,835,084
Issued: Dec. 28, 2004
Appl. No.: 10/366,912
Filed: Feb. 14, 2003

Related U.S. Application Data

(60) Provisional application No. 60/357,360, filed on Feb. 15, 2002.

(51) Int. Cl.
*H01R 13/627* (2006.01)

(52) U.S. Cl.
USPC .......................................... 439/349; 439/352

(58) Field of Classification Search
None
See application file for complete search history.

(56) References Cited

To view the complete listing of prior art documents cited during the proceeding for Reexamination Control Number 90/012,027, please refer to the USPTO's public Patent Application Information Retrieval (PAIR) system under the Display References tab.

*Primary Examiner* — Hetul Patel

(57) ABSTRACT

A medically implantable electrical connector includes a housing having a bore with an internal V-groove or a flat bottom groove therein along with radial garter spring disposed in the V-groove or an axial garter spring disposed in the flat bottom groove. A pin is provided and sized for insertion in the housing bore. The housing, spring and pin are formed from a combination of medically implantable materials in order to control electrical resistivity between the housing, the garter spring and the pin.

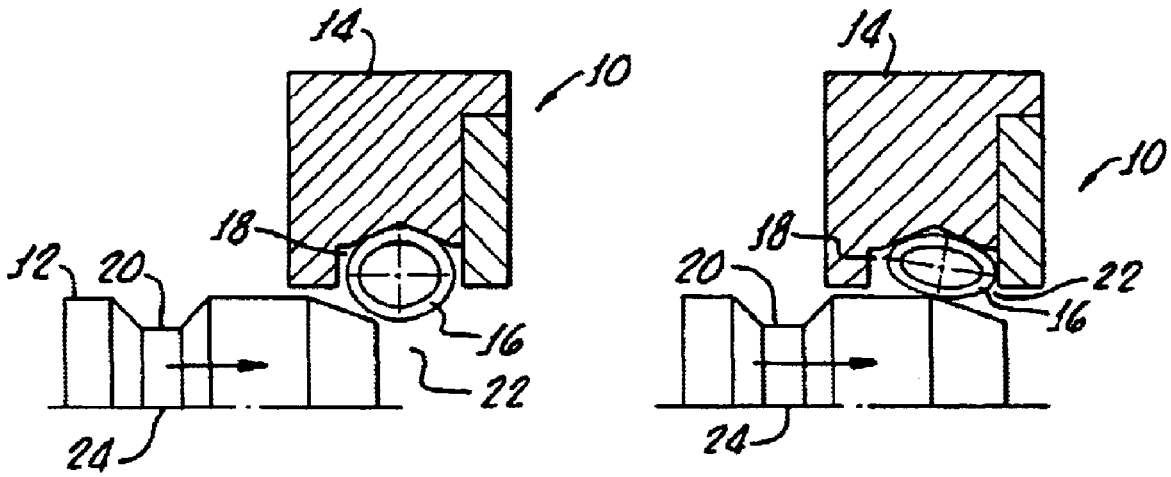

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-8 and 15-20 is confirmed.

Claims 9-14 are cancelled.

New claims 21-59 are added and determined to be patentable.

21. The connector according to claim 1, wherein the V-groove comprises two sidewalls and wherein said radial garter spring is spaced from said two sidewalls.

22. The connector according to claim 21, wherein the pin includes an external V-groove and wherein the spring contacts the V-groove of the housing and the V-groove of the pin.

23. The connector according to claim 1, wherein the pin is movable in a first direction to connect the pin to the housing and movable in a second direction, opposite the first direction, to disconnect the pin from the housing.

24. A medically implantable electrical connector comprising:
   a housing having a bore with an internal flat bottomed groove therein;
   an axial garter spring disposed in said groove; and
   a pin sized for insertion into the housing bore;
   said housing, spring and pin being formed from a combination of medically implantable materials in order to control electrical resistivity between said housing, said garter spring and said pin; and wherein the pin is without a groove.

25. The connector according to claim 24, wherein the pin is movable in a first direction to connect the pin to the housing and movable in a second direction, opposite the first direction, to disconnect the pin from the housing.

26. The connector according to claim 24, wherein the flat bottomed groove is located in between two sidewalls and wherein the spring simultaneously contacts the flat bottomed groove and the two sidewalls.

27. The connector according to claim 15, wherein the housing further comprises two sidewalls in the V-groove and wherein the radial garter spring is spaced from the two sidewalls.

28. The connector according to claim 15, wherein the pin is movable in a first direction to connect the pin to the housing and movable in a second direction, opposite the first direction, to disconnect the pin from the housing.

29. A medically implantable electrical connector comprising:
   a housing having a bore with an internal flat bottomed groove therein;
   an axial garter spring disposed in said groove;
   a pin sized for insertion into the housing bore by moving the pin in a first direction so that the axial garter spring simultaneously contacts the internal flat bottomed groove of the housing and a side surface of the pin without a pin groove, and wherein the pin is removable from the housing when moved in a second direction opposite the first direction; and
   said housing, spring and pin being formed from a combination of medically implantable materials such that electrical resistivity between said housing, said garter spring and said pin is lower in value than when said housing is made from stainless steel.

30. The connector according to claim 29, wherein the flat bottomed groove comprises two sidewalls and wherein said axial garter spring simultaneously contacts said two sidewalls and said flat bottomed groove.

31. The connector according to claim 29, wherein one of said housing, said garter spring and said pin is formed from platinum iridium.

32. A medically implantable electrical connector with latching and unlatching comprising:
   a housing having a bore with an internal V-groove therein;
   a radial garter spring disposed in said V-groove; and
   a pin comprising a V-groove having a diameter sized for insertion into the housing bore to simultaneously contact the radial garter spring between the V-groove of the housing and the V-groove of the pin;
   said housing, spring and pin being formed from a combination of medically implantable materials comprising platinum-iridium and MP35N in order to control electrical resistivity between said housing, said garter spring and said pin.

33. The connector according to claim 32, wherein said V-groove of said housing comprises two sidewalls and wherein said radial garter spring is spaced from said two sidewalls.

34. The connector according to claim 32, wherein said V-groove of said pin comprises a flat center portion subtended by angled sides of said V-groove.

35. A medically implantable electrical connector with latching and unlatching comprising:
   a housing having a bore with an internal V-groove therein;
   a radial garter spring disposed in said V-groove; and
   a pin sized for insertion into the housing bore, said pin including an external groove comprising a flat bottomed groove or two tapered surfaces converging to a point for capturing said spring in order to removably latch said pin within the housing bore, said latch providing a disconnect force and a connect force; and
   said housing, spring and pin being formed from a combination of medically implantable materials in order to control electrical resistivity between said housing, said garter spring and said pin.

36. A medically implantable electrical connector comprising:
   a housing having a bore with an internal V-groove therein with two sidewalls;
   a radial garter spring disposed in said V-groove and spaced from said two sidewalls; and
   a pin sized for insertion into the housing bore;
   said housing, spring and pin being formed from a combination of medically implantable materials comprising platinum-iridium and MP35N in order to control electrical resistivity between said housing, said garter spring and said pin.

37. The connector according to claim 36, wherein the pin includes an external V-groove and wherein the radial garter spring contacts the V-groove of the housing and the V-groove of the pin.

38. The connector according to claim 36, wherein the pin comprises a groove with a flat center portion subtended by angled sides.

39. The connector according to claim 1, wherein said radial garter spring simultaneously contacts both slanted surfaces of the V-groove.

40. The connector according to claim 1. wherein said pin is without an external groove.

41. The connector according to claim 15, wherein the radial garter spring simultaneously contacts both slanted surfaces of the V-groove of the housing and the external groove of the pin.

42. The connector according to claim 24, wherein said housing, spring and pin are formed from a combination of medically implantable materials comprising platinum-iridium and MP35N.

43. The connector according to claim 24, wherein the housing flat bottomed groove comprises two sidewalls and wherein the axial garter spring simultaneously contacts the flat bottomed groove and the two sidewalls.

44. The connector according to claim 24, wherein said housing and pin are formed from MP35N.

45. The connector according to claim 24, wherein said housing and pin are formed from titanium grade-5.

46. The connector according to claim 24, wherein one of said housing, said axial garter spring, and said pin is formed from platinum iridium.

47. The connector according to claim 29, wherein one of said housing, said garter spring and said pin is formed from platinum iridium.

48. The connector according to claim 29, wherein said housing and pin are formed from MP35N.

49. The connector according to claim 29, wherein said housing and pin are formed from titanium grade-5.

50. The connector according to claim 32, wherein said radial garter spring simultaneously contacts both slanted surfaces of the V-groove of the housing.

51. The connector according to claim 32, wherein said spring is made from platinum-iridium and said housing is made from MP35N.

52. The connector according to claim 51, wherein said pin is made from MP35N.

53. The connector according to claim 32, wherein said housing is made from platinum-iridium.

54. The connector according to claim 35, wherein a ratio of disconnect force to connect force is between about 1.3 to 1 and about 10 to 1.

55. The connector according to claim 53, wherein the radial garter spring simultaneously contacts the V-groove of the housing and the V-groove of the pin.

56. The connector according to claim 35, wherein said spring is made from platinum-iridium and said housing is made from MP35N.

57. The connector according to claim 35, wherein said pin is made from MP35N.

58. The connector according to claim 35, wherein said housing is made from platinum-iridium.

59. The connector according to claim 35. wherein said housing, spring and pin are formed from a combination of medically implantable materials comprising platinum-iridium and MP35N.

* * * * *